United States Patent [19]

Kaiser et al.

[11] 4,301,045

[45] Nov. 17, 1981

[54] SYNTHESIS OF PEPTIDES

[75] Inventors: Emil Kaiser, Chicago; Robert L. Colescott, Bourbonnais, both of Ill.

[73] Assignee: Armour Pharmaceutical Company, Kankakee, Ill.

[21] Appl. No.: 792,524

[22] Filed: May 2, 1977

[51] Int. Cl.³ .................... C08L 37/00; C07C 103/52
[52] U.S. Cl. .................. 260/8; 260/112.5 R
[58] Field of Search ............. 260/112.5 R, 8

[56] References Cited

U.S. PATENT DOCUMENTS

| | | | |
|---|---|---|---|
| 3,531,258 | 9/1970 | Merrifield et al. | 260/112.5 R |
| 3,743,628 | 7/1973 | Bodanszky et al. | 260/112.5 R |
| 3,886,132 | 5/1975 | Brewer et al. | 260/112.5 R |
| 3,912,711 | 10/1975 | Leeman et al. | 260/112.5 R |
| 3,915,949 | 10/1975 | Colescott et al. | 260/112.5 R |
| 3,917,579 | 11/1975 | Bumpus et al. | 260/112.5 R |
| 3,987,014 | 10/1976 | Guiducci et al. | 260/112.5 R |
| 3,988,307 | 10/1976 | Gross | 260/112.5 R |
| 4,002,740 | 1/1977 | Goldstein et al. | 260/112.5 R |
| 4,022,760 | 5/1977 | Tinney | 260/112.5 R |

OTHER PUBLICATIONS

R. B. Merrifield, "The Chemical Innovators", 15, 1971, pp. 22-25.
R. B. Merrifield, "Solid-Phase Peptide Synthesis", pp. 242-251.
J. Stewart, et al., Solid Phase Peptide Synthesis, 1969, pp. 2-5 & 19-20.

*Primary Examiner*—Delbert R. Phillips
*Attorney, Agent, or Firm*—Carl C. Batz; Edmond T. Patnaude

[57] ABSTRACT

Resin peptides useful in the preparation of peptides having biological activity, and particularly such resin peptides containing Pro—Asp—CH₂—Ⓡ or Pro—Asn—CH₂—Ⓡ at one of an amino acid chain, Ⓡ being the resin and Pro, Asp and Asn being the residues of the amino acids proline, aspartic acid and asparagine; and processes for the preparation of such resin peptides.

10 Claims, No Drawings

SYNTHESIS OF PEPTIDES

This invention relates to the synthesis of peptides and particularly resin peptides which are useful in the production of biologically active peptides. The invention involves such peptides as new compounds and also processes by which they may be produced.

BACKGROUND

The adrenocorticotropic hormone (ACTH) has been identified by T. H. Lee, A. B. Lerner and V. B. Buettner, *Janusch J. Biol. Chem.*, 236, 2970 (1961) as having a sequence of 39 amino acids, its amino-terminal 1–25 sequence having the following structure:

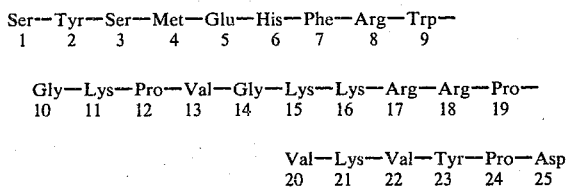

Abbreviations Phe, Glu, Leu, etc. stand for the different amino acid groupings in the peptide chain and the numbers represent the positions of the amino groups in the chain according to accepted nomenclature.

It is a principal object of this invention to discover intermediate resin peptides from which biologically active peptides may be derived, particularly peptides with adrenocorticotropic hormone activity, and to provide effective processes for the commercial production of such peptides. Other more specific objects will become apparent as this specification proceeds.

We are aware of disclosures of certain laboratory methods for the synthesis of certain peptides of relatively short amino acid chain lengths. These include an article by R. B. Merrifield entitled "*Solid Phase Peptide Synthesis.*" I. "*The Synthesis of a Tetrapeptide*" at pages 2149 to 2154 in Vol. 85 of *Journal of the American Chemical Society* (1963) and a book entitled "*Solid Phase Peptide Synthesis*" by John W. Stewart and Janis D. Young published by W. H. Freeman and Company of San Francisco, Calif., but find in these publications no disclosures of resin peptides having amino groups of the kind and in the sequence involved in the present invention.

DESCRIPTION OF INVENTION

Our total synthesis involves many reactions by which many new intermediate resin peptides are formed and we will proceed with the description step by step, giving the structural formula, the general description and specific examples as we proceed.

In general, we utilize a solid phase synthesis whereby an insoluble polystyrene resin, obtained by catalytic polymerization of styrene and divinyl benzene, is chloromethylated.

To the chloromethylated resin, we couple first aspartic acid, then proline and the other amino acids of the chain, is prescribed sequence, using a system of protection and deprotection of the active amino and carboxyl groups. Following the coupling of the last amino acid in the chain, the resin is cleaved from the peptide chain and the remaining protective groups removed. All amino acids are the naturally occurring L-isomers unless specifically defined.

PREPARATION OF INSOLUBLE RESIN

An insoluble resin, hereinafter identified by the symbol ®, is a polymeric material which is insoluble in, but solvated and penetrated by the solvents used in peptide synthesis and is capable of providing an active receptor site for the first amino acid herein, namely, aspartic acid.

In practice, we find that we prefer to use an insoluble polystyrene resin obtained by the catalytic polymerization of styrene and divinyl benzene. The resin is chloromethylated using chloromethylmethyl ether and stannic chloride catalyst according to the following reaction formula:

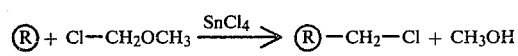

The chloromethylation reaction is specifically illustrated by the following Example 1.

EXAMPLE 1

One Kg. of 2% divinylbenzene crosslinked polystyrene resin 200–400 mesh was washed with three 2 liter portions of methylene chloride. Fine particles were removed by draining the methylene chloride off the bottom each time. The resin was washed with two liters of the following solvents by suspension, stirring for 10 minutes and filtration on a sintered glass Buchner: Two portions tetrahydrofuran, 2 portions water, 1 portion normal sodium hydroxide, 2 portions water, 2 portions dimethylformamide, 2 portions dioxane and 3 portions methanol. This washed resin was dried under vacuum at 60° C.

Five hundred grams of this washed polystyrene resin was stirred with 5 liters of chloromethyl methyl ether at room temperature and then the temperature was lowered to 0°–5° C. with an ice-water bath. Seventy-five grams of anhydrous stannic chloride in 925 ml. ice-cold chloromethyl methyl ether was added and the mixture stirred in the ice-bath for 2 hours. The resin was filtered on a sintered glass Buchner and then washed with 2 liter portions of the following solvents: 25% water in dioxane, 25% two normal hydrochloric acid in dioxane, water and twice with methanol. The washed resin was dried under vacuum at 45°–50° C. By this method, the usual chloride content is between 0.7 to 1.0 milliequivalent per gram.

ASPARTIC ACID ESTERIFICATION TO THE POLYSTYRENE RESIN

By our synthesis, aspartic acid is first bonded to the polystyrene resin. This is described by the following formula:

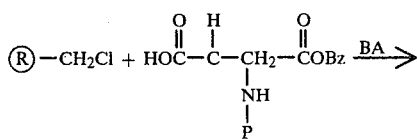

-continued

Coupling Reaction No. 1

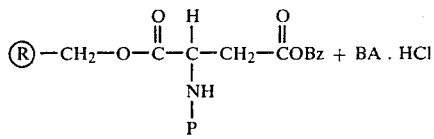 + BA . HCl where Ⓡ is divinylbenzene crosslinked polystyrene resin, BA is a suitable base such as triethylamine, diisopropylamine, diisopropylethylamine, or alkali metal salt, and "P" is an amino protective group which preferably is tertiary-butyloxy-carbonyl (BOC), but may be amyloxycarbonyl (AMOC) or ortho-nitrophenylsulfenyl (NPS) and Bz is benzyl or benzyl derivative. "Benzyl derivative" as used herein indicates those derivatives of the benzyl radical such as benzyl, p-methoxybenzyl, p-chlorobenzyl, p-nitrobenzyl or benzylhydroxyl or equivalents thereof, and these derivatives are well known to the peptide chemist.

As illustrated by the above formula, the tert-butyloxycarbonyl-L-beta-benzylaspartate is attached to the chloromethylated resin in the presence of an acid acceptor. This reaction is demonstrated by the following specific Example 2.

EXAMPLE 2

Five (5) grams of chloromethylated polystyrene resin, prepared as illustrated previously with a chlorine content of 0.74 milliequivalent (meq) per gram (3.7 meq chlorine) and 2.5 grams BOC-L-beta-benzylaspartate (7.4 meq) was stirred in 25 ml of absolute ethyl alcohol and then 0.99 ml of triethylamine (7.2 meq) was added and the mixture refluxed with stirring for 24 hours. The mixture was cooled, filtered on a sintered glass Buchner and washed on the Buchner with 100 ml portions of the following solvents: 2 times with 3A denatured alcohol, 2 times with dioxane, 2 times with 3A denatured alcohol, 2 times with water and 2 times with methanol. The resin was dried under vacuum at 40°–45° C. When the BOC protecting group was removed with hydrochloric acid saturated dioxane as hereinafter described and the resin titrated to determine the available terminal amine group, this sample was found to approximate 0.38 meq per gram.

Deprotection and Neutralization

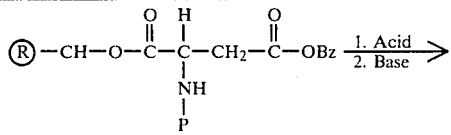 $\xrightarrow{\text{1. Acid} \atop \text{2. Base}}$

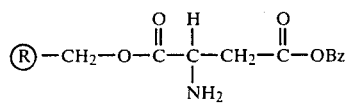

This resulting product is designated "Compound No. 1".

The deprotection of the amine function of the benzylaspartate is accomplished by the removal of the protecting group using a suitable acid such as trifluoroacetic acid or hydrochloric acid. The resulting amine salt is then neutralized by treatment with a strong organic base. A specific example of this procedure is given in the following Example 3.

EXAMPLE 3

A one gram sample of the BOC-benzylaspartate resin, as prepared by Example 2, was placed in the reaction vessel of a peptide synthesizer. The sample was washed twice with 20 ml portions of trichloroethylene for two minutes each. A mixture of 10 ml hydrogen chloride saturated dioxane and 10 ml. of trichloroethylene was added and the mixture reached for 20 minutes. After filtration, the resin was washed with three 20 ml. portions of chloroform, 2 portions of methanol and 2 portions of chloroform, each wash being of 2 minute duration. Neutralization was accomplished by a 10 minute reaction with 20 ml. of a 10% solution of triethylamine in chloroform. The resin was then washed 3 times with 20 ml. of chloroform and 3 times with 20 ml. of methylene chloride.

Coupling of Second Amino Acid

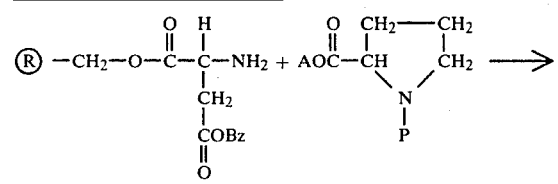

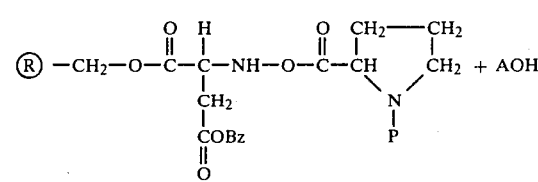 + AOH

Or

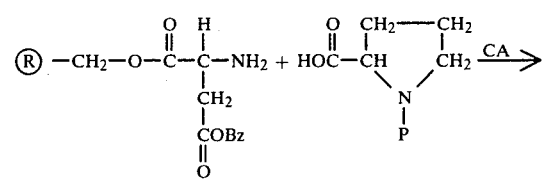

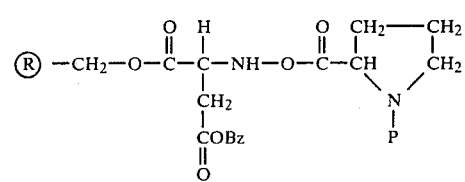

Compound No. 2

In these formulae, "P" is an amino protective group, as described previously, "A" is an active ester such as p-nitrophenyl, o-nitrophenyl or penta-chlorophenyl, "CA" is a coupling agent which is preferably dicyclohexylcarbodiimide (DCC), but may be any coupling agent which forms peptide bonds, such as diimides, azides or mixed anhydrides. The symbols Ⓡ, P, A and CA are to be taken as having the meanings above defined whenever they appear in the specifications and claims.

Since the formula described previously begins to be cumbersome, we may rewrite the formula of the reaction product in the following manner:

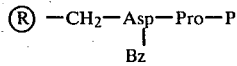

wherein, "Asp" stands for aspartic acid residue, "Pro" stands for the proline residue and P and Bz are as previously defined. This simplified nomenclature will be utilized in the description of all subsequent reactions.

In the literature pertaining to peptides it has become customary that the amino acid chain be written with the amino function at the left and the carboxyl function at the right, so this reaction product may be written:

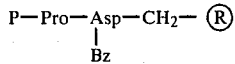

wherein P is BOC, AMOC, or NPS, and Bz is benzyl, p-methoxybenzyl, p-chlorobenzyl, p-nitrobenzyl, benzylhydryl, or equivalents thereof.

Deprotection and neutralization as explained in connection with the aspartate resin, results in a product bearing the following formula:

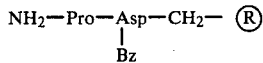

We believe that this resin peptide was made for the first time by our invention, and that this is an important link in the synthesis of the hormone ACTH fragment.

Further, we believe it is important that the coupling reaction is complete and have found the Ninhydrin test, described by E. Kaiser, R. Colescott, C. D. Bossinger, and P. Cook in *Anal. Biochem.*, 34, 595–98 (1970), to be applicable to determine when the coupling reaction is sufficiently complete. If the Ninhydrin test is negative, we may proceed to the deprotection of the resin peptide and go on to the following coupling reaction. If this test is positive, we repeat the coupling step until the Ninhydrin test result is finally negative.

Following are specific examples of the coupling of proline.

EXAMPLE 4

To a deprotected beta-benzylaspartate resin prepared according to Example 3 and having 0.38 meq of amine group was added a solution of 0.8 millimoles (approx. 100% excess) of o-nitrophenylsulfenyl proline (NPS-Pro) in 20 ml. of methylene chloride. After two minutes, a solution of 0.8 meq of dicyclohexylcarbodiimide (DCC) was added and the mixture agitated for 45 minutes. The product was filtered and washed three times each with 20 ml. portions of methylene chloride, methanol and trichloroethylene. The Ninhydrin test was performed on a 3-5 mg. sample of resin peptide reaction product and found to be negative. This resin was then deprotected as was described in Example 3.

EXAMPLE 5

Two grams beta-benzylaspartate resin was deprotected and neutralized as described in Example 3. Two millimoles of BOC-proline dissolved in 20 ml. of methylene chloride was added followed by 2 millimoles of dicyclohexylcarbodiimide. The mixture was agitated for one hour, filtered and washed with two portions of methylene chloride, two portions of methanol and three portions of methylene chloride.

EXAMPLE 6

In place of the BOC derivative in Example 5, we may substitute the AMOC derivative in the same meq amounts and the same results may be obtained.

EXAMPLE 7

One gram of beta-benzylaspartate resin was deprotected and neutralized as described in Example 3, washed three times with 20 ml. of dimethylformamide and shaken for 20 hours with 3.0 meq of BOC-proline-p-nitrophenyl ester dissolved in 20 ml. of dimethylformamide. The product was washed with two portions of dimethylformamide, two portions of methylene chloride, two portions of methanol and three portions of trichloroethylene.

EXAMPLE 8

In place of the p-nitrophenyl ester of Example 7, ortho-nitrophenyl ester, pentachlorophenyl ester or other active esters may be substituted and the reaction carried out as set forth in Example 7.

SYNTHESIS OF PEPTIDE

The following Table 1 lists in sequence the amino acids attached at each of reactions 2 to 25, indicating the position in the chain in which the attachment is made and listing the reactant used with the preferred protecting groups.

TABLE 1

| Reaction Number | Position Number | Amino Acid Being Attached | Amino Acid Group With Preferred Protectants |
|---|---|---|---|
| 2 | 24 | proline | BOC-L-proline |
| 3 | 23 | tyrosine | BOC-L-tyrosine |
| 4 | 22 | valine | BOC-L-valine |
| 5 | 21 | lysine | BOC-epsilon-trifluoro-acetyl-L-lysine |
| 6 | 20 | valine | BOC-L-valine |
| 7 | 19 | proline | BOC-L-proline |
| 8 | 18 | arginine | BOC-L-tosylarginine |
| 9 | 17 | arginine | BOC-L-tosylarginine |
| 10 | 16 | lysine | BOC-epsilon-trifluoro-acetyl-L-lysine |
| 11 | 15 | lysine | BOC-epsilon-trifluoro-acetyl-L-lysine |
| 12 | 14 | glycine | BOC-glycine |
| 13 | 13 | valine | BOC-L-valine |
| 14 | 12 | proline | BOC-L-proline |
| 15 | 11 | lysine | BOC-epsilon-trifluoro-acetyl-L-lysine |
| 16 | 10 | glycine | BOC-glycine |
| 17 | 9 | tryptophan | BOC-L-tryptophan |
| 18 | 8 | arginine | BOC-L-tosylarginine |
| 19 | 7 | phenylalanine | BOC-L-phenylalanine |
| 20 | 6 | histidine | BOC-im-carbobenzyloxy-L-histidine |
| 21 | 5 | glutamic acid | BOC-L-benzylglutamate |
| 22 | 4 | methionine | BOC-L-methionine |
| 23 | 3 | serine | BOC-O-benzyl-L-serine |
| 24 | 2 | tyrosine | BOC-L-tyrosine |
| 25 | 1 | serine | BOC-O-benzyl-L-serine |

As was described in connection with the attachment of proline in Reaction No. 2, (see Example 5), each succeeding reaction to attach another amino acid group involves the general procedure in which the resin peptide previously prepared is coupled with another protected amino acid derivative. The newly coupled peptide is then deprotected and neutralized. More specifically, the following steps may in the case of each reaction be as follows:

Coupling:
0.8 millimoles of the appropriate amino acid (100% equivalent excess in 15 ml. of methylene chloride or DMF mixture where required).
0.8 millimoles of dicyclohexylcarbodiimide (coupling agent) in 5 ml. of methylene chloride—45 minutes reaction time.
3×20 ml. methylene chloride washes—2 minutes each.
2×20 ml. methanol washes—2 minutes each.
3×20 ml. trichloroethylene washes—2 minutes each.

Deprotection:
10 ml. hydrogen chloride saturated dioxane plus 10 ml. trichloroethylene—20 minutes.
(After Reaction No. 16, 1% 2-mercaptoethanol or ethanedithiol is added to the acid saturated dioxane mixture.)
2×20 ml. chloroform washes—2 minutes each.
2×20 ml. methanol washes—2 minutes each.
3×20 ml. chloroform washes—2 minutes each.

Neutralization:
20 ml. 10% triethylamine in chloroform—10 minutes.
3×20 ml. chloroform washes—2 minutes each.
3×20 ml. methylene chloride washes—2 minutes each.

As previously stated, Compound No. 3, which is the result of reaction No. 3 (after deprotection and neutralization) is:

$$NH_2-Tyr-Pro-Asp-CH_2-\text{®} \quad (3)$$
$$\phantom{NH_2-}\;\;\;|\phantom{yr-Pro-}\;|$$
$$\phantom{NH_2-Tyr}Y\phantom{-Pro-}Bz$$

in which Bz is benzyl, p-methoxybenzyl, p-chlorobenzyl, p-nitrobenzyl or benzylhydryl, and Y is hydrogen, Bz, or 2-bromocarbobenzyloxy.

Compound No. 4, which is the result of reaction No. 4, is:

$$NH_2-Val-Tyr-Pro-Asp-CH_2-\text{®} \quad (4)$$
$$\phantom{NH_2-Val-}\;|\phantom{yr-Pro-}\;|$$
$$\phantom{NH_2-Val-Tyr}Y\phantom{-Pro-}Bz$$

in which Bz and Y are the same as in Compound No. 3.

Where lysine is attached, in reaction No. 5, position No. 21 we prefer to use as the epsilon amine protection agent trifluoroacetyl (TFA) but may also use carbobenzyloxy (CBZ), 2-bromocarbobenzyloxy, 2,4-dichlorocarbobenzyloxy or 2-chlorocarbobenzyloxy (Cl-CBZ). We use the symbol V to indicate epsilon protection agent in one of these named groups.

The coupling at position No. 21, followed by the usual deprotection and neutralization, results in the resin peptide represented by the following formula:

$$NH_2-Lys-Val-Tyr-Pro-Asp-CH_2-\text{®}$$
$$\phantom{NH_2-}\;|\phantom{ys-Val-}\;|\phantom{yr-Pro-}\;|$$
$$\phantom{NH_2-Lys}V\phantom{-Val-Tyr}Y\phantom{-Pro-}Bz$$

For the coupling of the arginine amino acid in reaction No. 8 at position No. 18, we prefer to use as the guanidino protection agent the tosyl group (p-toluene sulfonyl), but may use a nitro group, and in the formula of this specification, we employ the symbol "T" to mean nitro or tosyl.

The coupling of arginine at position no. 18, followed by the usual deprotection and neutralization, results in the resin peptide represented by the following formula:

$$NH_2-Arg-Pro-Val-Lys-Val-Tyr-Pro-Asp-CH_2-\text{®}$$
$$\phantom{NH_2-}\;|\phantom{rg-Pro-Val-}\;|\phantom{ys-Val-}\;|\phantom{yr-Pro-}\;|$$
$$\phantom{NH_2-Arg}T\phantom{-Pro-Val-Lys}V\phantom{-Val-Tyr}Y\phantom{-Pro-}Bz$$

in which V, Y, and Bz are the same as compound No. 5 and T is as above stated.

For the coupling of the histidine in reaction No. 20 at position No. 6, we prefer to use as the imidazole protection agent the carbobenzyloxy group (CBZ), but may use tosyl, dinitrophenyl, benzyl, benzyl derivative or no protecting group. We use the symbol W to indicate either or any of the above named derivatives.

The coupling of histidine in reaction No. 20, Position No. 6, followed by the usual deprotection and neutralization, results in the resin peptide represented by the following formula:

$$NH_2-His-Phe-Arg-Trp-Gly-Lys-Pro-Val-Gly-$$
$$\phantom{NH_2-}\;|\phantom{is-Phe-}\;|\phantom{rg-Trp-Gly-}\;|$$
$$\phantom{NH_2-His}W\phantom{-Phe-}T\phantom{-Trp-Gly-Lys}V$$
$$Lys-Lys-Arg-Arg-Pro-Val-Lys-Val-Tyr-$$
$$\;|\phantom{ys-}\;|\phantom{ys-}\;|\phantom{rg-}\;|\phantom{rg-Pro-Val-}\;|\phantom{ys-Val-}\;|$$
$$V\phantom{ys-}V\phantom{ys-}T\phantom{rg-}T\phantom{rg-Pro-Val-Lys}V\phantom{-Val-}Y$$
$$\phantom{Lys-Lys-Arg-Arg-Pro-Val-Lys-}Pro-Asp-CH_2-\text{®}$$
$$\phantom{Lys-Lys-Arg-Arg-Pro-Val-Lys-Val-Pro-}|$$
$$\phantom{Lys-Lys-Arg-Arg-Pro-Val-Lys-Val-Pro-}Bz$$

in which T, V, Y and Bz are the same as in compound No. 5 and W is as above stated.

After each coupling reaction, and before deprotection of the resin peptide, we apply the Ninhydrin test. If the test is "positive", the coupling reaction last performed is repeated. If the test is "negative", we proceed to the deprotection of the resin peptide.

Upon the attachment of serine in reaction 25 at the No. 1 position, according to the manner and sequence above described, and after the deprotection and neutralization of the coupled resin peptide, we arrive at Compound No. 25 which has the following formula:

$$NH_2-Ser-Tyr-Ser-Met-Glu-His-Phe-Arg-Trp-$$
$$\phantom{NH_2-}\;|\phantom{er-}\;|\phantom{yr-}\;|\phantom{er-Met-Glu-}\;|\phantom{is-Phe-}\;|$$
$$\phantom{NH_2-Ser}Bz\phantom{-}Y\phantom{-}Bz\phantom{-Met-Glu-}Bz\phantom{-is-}W\phantom{-Phe-}T$$
$$Gly-Lys-Pro-Val-Gly-Lys-Lys-Arg-Arg-Pro-$$
$$\phantom{Gly-}\;|\phantom{ys-Pro-}\;|\phantom{al-Gly-}\;|\phantom{ys-}\;|\phantom{ys-}\;|\phantom{rg-}\;|$$
$$\phantom{Gly-Lys}V\phantom{-Pro-Val-Gly-Lys}V\phantom{ys-}V\phantom{ys-}T\phantom{rg-}T$$
$$\phantom{Gly-Lys-Pro-Val-Gly-Lys-}Val-Lys-Val-Tyr-Pro-Asp-CH_2-\text{®}$$
$$\phantom{Gly-Lys-Pro-Val-Gly-Lys-Val-}|\phantom{ys-Val-}\;|\phantom{yr-Pro-}\;|$$
$$\phantom{Gly-Lys-Pro-Val-Gly-Lys-Val-}V\phantom{-Val-}Y\phantom{-Pro-}Bz$$

in which W, T, V, Y and Bz are the same as in Compound No. 20.

The resin peptides may then be treated to remove the resin and the protective groups as described in Examples 8 and 9. Suitably, the resin and most or all of the remaining protective groups may be removed by treatment with anhydrous hydrogen fluoride.

When V is carbobenzyloxy (CBZ), 2-bromocarbobenzyloxy, 2,4-dichlorocarbobenzyloxy or 2-chlorocarbobenzylloxy (Cl-CBZ), (Compound 25), the reaction may be represented as follows:

Reaction No. 26

$$NH_2-Ser-Tyr-Ser-Met-Glu-His-Phe-Arg-Trp-$$
$$\phantom{NH_2-}\;|\phantom{er-}\;|\phantom{yr-}\;|\phantom{er-Met-Glu-}\;|\phantom{is-Phe-}\;|$$
$$\phantom{NH_2-Ser}Bz\phantom{-}Y\phantom{-}Bz\phantom{-Met-Glu-}Bz\phantom{-is-}W\phantom{-Phe-}T$$

-continued

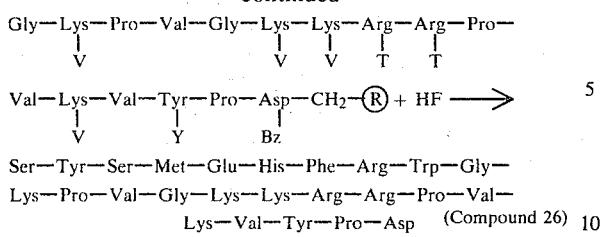

```
Ser—Tyr—Ser—Met—Glu—His—Phe—Arg—Trp—Gly—
Lys—Pro—Val—Gly—Lys—Lys—Arg—Arg—Pro—Val—
                Lys—Val—Tyr—Pro—Asp      (Compound 26)
```

When V is TFA, the formula of the compound after reaction 26 may be written:

```
Ser—Tyr—Ser—Met—Glu—His—Phe—Arg—Trp—Gly—
Lys—Pro—Val—Gly—Lys—Lys—Arg—Arg—Pro—Val—
 |            |   |
TFA          TFA TFA
Lys—Val—Tyr—Pro—Asp         (Compound 26a)
 |
TFA
```

EXAMPLE 8

This example illustrates the cleavage reaction when V is carbobenzyloxy, 2-bromocarbobenzyloxy, 2,4-dichlorocarbobenzyloxy or chlorocarbobenzyloxy. Four-tenths of one gram of Compound 25 were placed in a Kel-F vessel with 1 ml. of anisole and 10 ml. of anhydrous hydrogen fluoride was added by distillation. This mixture was stirred at 0° C. for 1 hour. The hydrogen fluoride was removed by vacuum distillation, the residue washed four times with ethyl acetate followed by extraction with glacial acetic acid. The acetic acid extract was lyophilized to give 99 mg. of a fluffy white powder. This process removes the peptide from the resin and removes all protective groups on the amino acids. The product is Compound 26 and it has ACTH activity in the U.S.P. assay.

EXAMPLE 9

This example illustrates the cleavage reaction when "V" is trifluoroacetyl (TFA). Four-tenths of one gram of Compound 25 was placed in a Kel-F vessel with 1 ml. of anisole and 10 ml. of hydrogen fluoride was added by distillation. This mixture was stirred at 0° C. for 1 hour. The hydrogen fluoride was removed by vacuum distillation, the residue washed four times with ethyl acetate followed by extraction with glacial acetic acid. The acetic acid extract was lyophilized to give a fluffy white powder. This process removes the peptide from the resin and removes all blocking groups on the difunctional amino acids except the trifluoroacetyl (TFA) blocking group of the lysine residues. Hence, this product is called TFA-Peptide (Compound 26a). Three-tenths of a gram of TFA-Peptide was stirred for 3 hours in 5 ml. of 0.2 molar piperidine. This solution was then filtered and lyophilized. The compound formed was the same as Compound 26. Example 8 and had ACTH activity in the U.S.P. assay.

In the foregoing description aspartic acid was attached to the resin at reaction No. 1, position No. 25. We may substitute asparagine (Asn) instead of aspartic acid at this position, BOC-L-asparagine may be used as the reactant, and otherwise we may use the same conditions of reaction and the same sequence of amino acids as already described. In such case the compound obtained as a result of the series of reactions would be as follows:

Reaction No. 1

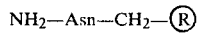

Reaction No. 2

Reaction No. 4

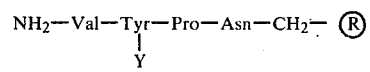

Reaction No. 5

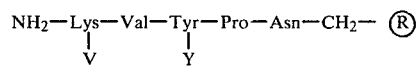

Reaction No. 8

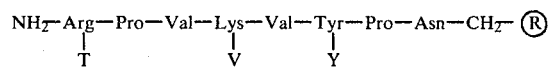

Reaction No. 20

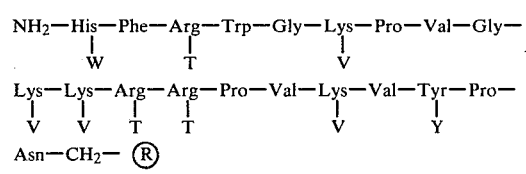

Reaction No. 25

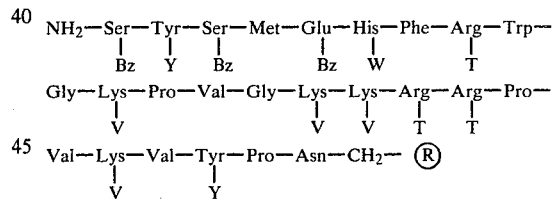

In the event that V is TFA after the cleavage of the resin compound by use of HF the compound where asparagine is attached at position No. 25 is represented by the following formula:

```
Ser—Tyr—Ser—Met—Glu—His—Phe—Arg—Trp—Gly—
Lys—Pro—Val—Gly—Lys—Lys—Arg—Arg—Pro—Val—
 |            |   |
TFA          TFA TFA
Lys—Val—Tyr—Pro—Asn
 |
TFA
```

EXAMPLE 10

A deprotected beta-benzyl aspartate resin,

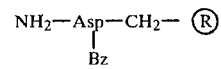

was prepared according to Example 2. One gram of this resin, containing 0.38 meq. amine per gram was used in the synthesis of a 1-25 ACTH peptide. The following BOC-amino acids were added sequentially.

Reaction 2
BOC-Amino Acid: 0.17 gm. BOC-proline.
Coupling Step: 20 ml. methylene chloride+0.2 gm. DCC. for 1 hour. Washings: 3×20 ml. methylenechloride, 3×20 ml. methanol, 3×20 ml. trichloroethylene.
Deprotection Step: 10 ml. dioxane saturated with HCl+10 ml. trichloroethylene for 20 minutes. Washings: 3×20 ml. chloroform, 3×20 ml. methanol, 3×20 ml. chloroform.
Removal of Acid: 10 ml. chloroform containing 10% triethylamine for 10 minutes. Washings: 2×20 ml. chloroform and 3×20 ml. methylene chloride.

Reaction 3
BOC-Amino Acid: 0.3 gm. BOC:O-benzyl-tyrosine.
Coupling Step: Same as Reaction 1
Deprotection Step: Same as Reaction 1
Removal of Acid: Same as Reaction 1

Reaction 4
BOC-Amino Acid: 0.17 gm. BOC-valine
Coupling Step: Same as Reaction 1
Deprotection Step: Same as Reaction 1
Removal of Acid: Same as Reaction 1

Reaction 5
BOC-Amino Acid: 0.3 gm. BOC-epsilon-CBZ-lysine
Coupling Step: Same as Reaction 1
Deprotection Step: Same as Reaction 1
Removal of Acid: Same as Reaction 1

Reaction 6
BOC-Amino Acid: 0.17 gm. BOC-valine
Coupling Step: Same as Reaction 1
Deprotection Step: Same as Reaction 1
Removal of Acid: Same as Reaction 1

Reaction 7
BOC-Amino Acid: 0.17 gm. BOC-proline
Coupling Step: Same as Reaction 1
Deprotection Step: Same as Reaction 1
Removal of Acid: Same as Reaction 1

Reaction 8
BOC-Amino Acid: 0.26 gm. BOC-nitroarginine
Coupling Step: 5 ml. dimethylformamide and 15 ml. methylene chloride for 1 hour. Washings: 3×20 ml. methylene chloride, 3×20 ml. methanol, 3×20 ml. trichloroethylene.
Deprotection Step: Same as Reaction 1
Removal of Acid: Same as Reaction 1

Reaction 9
BOC-Amino Acid: 0.25 gm. BOC-nitroarginine
Coupling Step: Same as Reaction 8
Deprotection Step: Same as Reaction 1
Removal of Acid: Same as Reaction 1

Reaction 10
BOC-Amino Acid: 0.3 gm. BOC-epsilon-CBZ-lysine
Coupling Step: Same as Reaction 1
Deprotection Step: Same as Reaction 1
Removal of Acid: Same as Reaction 1

Reaction 11
BOC-Amino Acid: 0.3 gm. BOC-epsilon-CBZ-lysine
Coupling Step: Same as Reaction 1
Deprotection Step: Same as Reaction 1
Removal of Acid: Same as Reaction 1

Reaction 12
BOC-Amino Acid: 0.14 gm. BOC-glycine
Coupling Step: Same as Reaction 1
Deprotection Step: Same as Reaction 1
Removal of Acid: Same as Reaction 1

Reaction 13
BOC-Amino Acid: 0.17 gm. BOC-valine
Coupling Step: Same as Reaction 1
Deprotection Step: Same as Reaction 1
Removal of Acid: Same as Reaction 1

Reaction 14
BOC-Amino Acid: 0.17 gm. BOC-proline
Coupling Step: Same as Reaction 1
Deprotection Step: Same as Reaction 1
Removal of Acid: Same as Reaction 1

Reaction 15
BOC-Amino Acid: 0.3 gm. BOC-epsilon-CBZ-lysine
Coupling Step: Same as Reaction 1
Deprotection Step: Same as Reaction 1
Removal of Acid: Same as Reaction 1

Reaction 16
BOC-Amino Acid: 0.14 gm. BOC-glycine
Coupling Step: Same as Reaction 1
Deprotection Step: Same as Reaction 1
Removal of Acid: Same as Reaction 1

Reaction 17
BOC-Amino Acid: 0.24 gm. BOC-tryptophane
Coupling Step: Same as Reaction 8
Deprotection Step: Same as Reaction 1+0.5% 2-mercaptoethanol
Removal of Acid: Same as Reaction 1

Reaction 18
BOC-Amino Acid: 0.26 gm. BOC-nitroarginine
Coupling Step: Same as Reaction 8
Deprotection Step: Same as Reaction 17
Removal of Acid: Same as Reaction 1

Reaction 19
BOC-Amino Acid: 0.21 gm. BOC-phenylalanine
Coupling Step: Same as Reaction 1
Deprotection Step: Same as Reaction 17
Removal of Acid: Same as Reaction 1

Reaction 20
BOC-Amino Acid: 0.28 gm. BOC-im-CBZ-histidine
Coupling Step: Same as Reaction 1
Deprotection Step: Same as Reaction 17
Removal of Acid: Same as Reaction 1

Reaction 21
BOC-Amino Acid: 0.28 gm. BOC-γ-benzylglutamate
Coupling Step: Same as Reaction 1
Deprotection Step: Same as Reaction 17
Removal of Acid: Same as Reaction 1

Reaction 22
BOC-Amino Acid: 0.2 gm. BOC-methionine
Coupling Step: Same as Reaction 1
Deprotection Step: Same as Reaction 17
Removal of Acid: Same as Reaction 1

Reaction 23
BOC-Amino Acid: 0.24 gm. BOC-O-benzyl-serine
Coupling Step: Same as Reaction 1
Deprotection Step: Same as Reaction 17
Removal of Acid: Same as Reaction 1

Reaction 24
BOC-Amino Acid: 0.30 gm. BOC-O-benzyl-tyrosine
Coupling Step: Same as Reaction 1
Deprotection Step: Same as Reaction 17
Removal of Acid: Same as Reaction 1

Reaction 25
BOC-Amino Acid: 0.24 gm. BOC-O-benzyl-serine
Coupling Step: Same as Reaction 1
Deprotection Step: Same as Reaction 17
Removal of Acid: Same as Reaction 1

The final resin peptide (1.5 gm.) when treated with HF as in Example 8 gave a biologically active 1-25 ACTH peptide. The activity of the crude product was 5 u./mg.

EXAMPLE 11

Five (5) grams of chloromethylated polystyrene resin was esterified with 7.4 meq. of BOC-asparagine in the same manner as described in Example 2 for the esterification with BOC-betz-benzyl-aspartate.

All other reactions were identical with those of Example 10 giving a 1-25 asparagine peptide with biological activity.

From the foregoing, it is apparent that methods and products have been herein described and illustrated which fulfill all of the foregoing objectives in a remarkably unexpected fashion. It is, of course, understood that the several examples herein presented are for explanatory and not limiting purposes, and such modifications, alterations and adaptions of this invention as may readily occur to the artisan in the light of this disclosure being within the spirit of this invention and the scope of the appended claims.

What is claimed is:

1. A resin peptide having the structure:

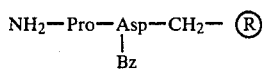

in which

Ⓡ is a crosslinked polystyrene resin, and Bz is benzyl, p-methoxybenzyl, p-chlorobenzyl, P-nitrobenzyl or benzhydryl.

2. A resin peptide having the structure:

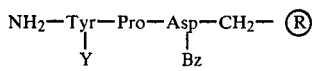

in which

R is a crosslinked polystyrene resin, Bz is benzyl, P-methoxybenzyl, p-chlorobenzyl, P-nitrobenzyl or benzhydryl, and Y is H or Bz.

3. A resin peptide having the structure:

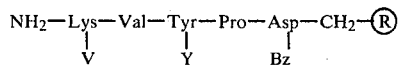

in which

Ⓡ is a crosslinked polystyrene resin and Bz is benzyl, p-methoxybenzyl, p-chlorobenzyl, P-nitrobenzyl or benzhydryl,
    Y is H or Bz
    and V is carbobenzyloxy, 2-chlorocarbobenzyloxy, 2-bromocarbobenzyloxy, dichlorocarbobenzyloxy or trifluoroacetyl.

4. A resin peptide having the structure:

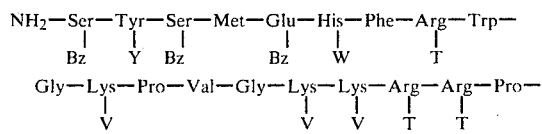
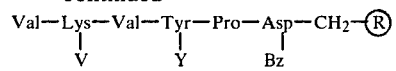

in which

R is a crosslinked polystyrene resin, and Bz is benzyl, p-methoxybenzyl, p-chlorobenzyl, p-nitrobenzyl or benzhydryl,
    Y is H or Bz,
    T is tosyl or nitro,
    W is carbobenzyloxy, tosyl, dinitrophenyl, Bz or H,
    and V is carbobenzyloxy, 2-chlorocarbobenzyloxy, 2-bromocarbobenzyloxy, dichlorocarbobenzyloxy or trifluoroacetyl.

5. A peptide having the structure:

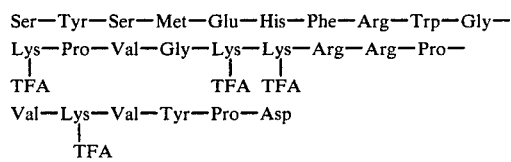

in which

TFA is trifluoroacetyl.

6. A resin peptide having the structure:

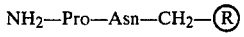

in which

R is a crosslinked polystyrene resin.

7. A resin peptide having the structure:

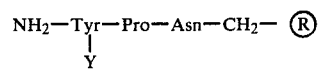

in which

R is a crosslinked polystyrene resin,
    and Y is H or Bz.

8. A resin peptide having the structure:

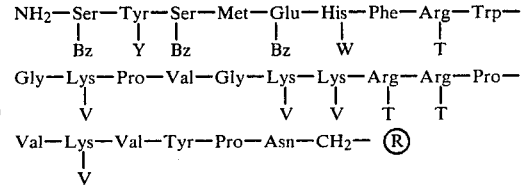

in which

Ⓡ is a crosslinked polystyrene resin, Bz is benzyl, p-methoxybenzyl, p-chlorobenzyl, p-nitrobenzyl or benzhydryl,
    Y is H or Bz,
    T is tosyl or nitro,
    W is carbobenzyloxy, tosyl, dinitrophenyl, Bz or H, and
    V is carbobenzyloxy, 2-chlorocarbobenzyloxy, 2-bromocarbobenzyloxy, dichlorocarbobenzyloxy or trifluoroacetyl.

9. A peptide having the structure:

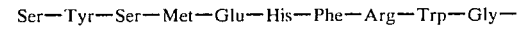

-continued
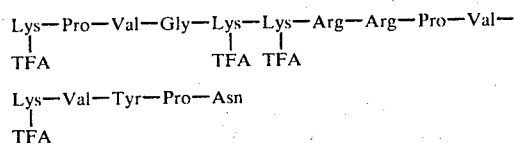
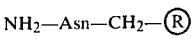
in which
TFA is trifluoroacetyl.
10. In a process for synthesizing a resin peptide, the step of coupling L-Pro-P with the reactant
NH₂—Asn—CH₂—(R)
or an active ester or an azide thereof, said coupling being conducted in the presence of a diimide unless said reactant is an active ester or an azide.
* * * * *